(12) United States Patent
Grenacher et al.

(10) Patent No.: US 6,723,884 B1
(45) Date of Patent: Apr. 20, 2004

(54) CONTINUOUS PROCESS FOR HYDROFORMYLATING OLEFINS WITH 6 TO 20 CARBON ATOMS

(75) Inventors: Armin Volker Grenacher, Mutterstadt (DE); Hans Stepp, Gönnheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/049,859

(22) PCT Filed: Aug. 18, 2000

(86) PCT No.: PCT/EP00/08095

§ 371 (c)(1),
(2), (4) Date: Feb. 19, 2002

(87) PCT Pub. No.: WO01/14297

PCT Pub. Date: Mar. 1, 2001

(30) Foreign Application Priority Data

Aug. 20, 1999 (DE) .......................................... 199 39 491

(51) Int. Cl.[7] .............................................. C07C 45/49
(52) U.S. Cl. ..................... 568/444; 568/451; 568/453
(58) Field of Search ................................ 568/444, 451, 568/453

(56) References Cited

U.S. PATENT DOCUMENTS

| | | | |
|---|---|---|---|
| 3,188,351 A | | 6/1965 | Lemke ........................ 260/604 |
| 3,929,898 A | * | 12/1975 | Nienburg et al. |
| 3,932,523 A | | 1/1976 | Strohmeyer et al. ........ 260/604 |
| 3,941,848 A | * | 3/1976 | Kummer et al. |
| 6,015,928 A | | 1/2000 | Gubisch et al. ............. 568/882 |

OTHER PUBLICATIONS

J. Falbe, *New Syntheses with Carbon Monoxide*, 1980, pp. 162–174.

* cited by examiner

*Primary Examiner*—Johann Richter
*Assistant Examiner*—Sikarl A. Witherspoon
(74) *Attorney, Agent, or Firm*—Keil & Weinkauf

(57) ABSTRACT

Olefins having from 6 to 20 carbon atoms are hydroformylated by means of a continuous process in which a) an aqueous cobalt(II) salt solution is brought into intimate contact with hydrogen and carbon monoxide to form a hydroformylation-active cobalt catalyst, and the aqueous phase comprising the cobalt catalyst is brought into intimate contact with the olefins and, if desired, an organic solvent and also hydrogen and carbon monoxide in at least one reaction zone where the cobalt catalyst is extracted into the organic phase and the olefins are hydroformylated, b) the output from the reaction zone is treated with oxygen in the presence of acidic aqueous cobalt(II) salt solution, with the cobalt catalyst being decomposed to form cobalt(II) salts and these being backextracted into the aqueous phase; and the phases are subsequently separated, c) the aqueous cobalt(II) salt solution is recirculated in unchanged form to step a), wherein the cobalt(II) salt solution has a concentration of from 1.1 to 1.7% by weight, calculated as cobalt, and is continually maintained under conditions under which the solubility limit of cobalt(II) formate in water is not exceeded.

Figure 1:
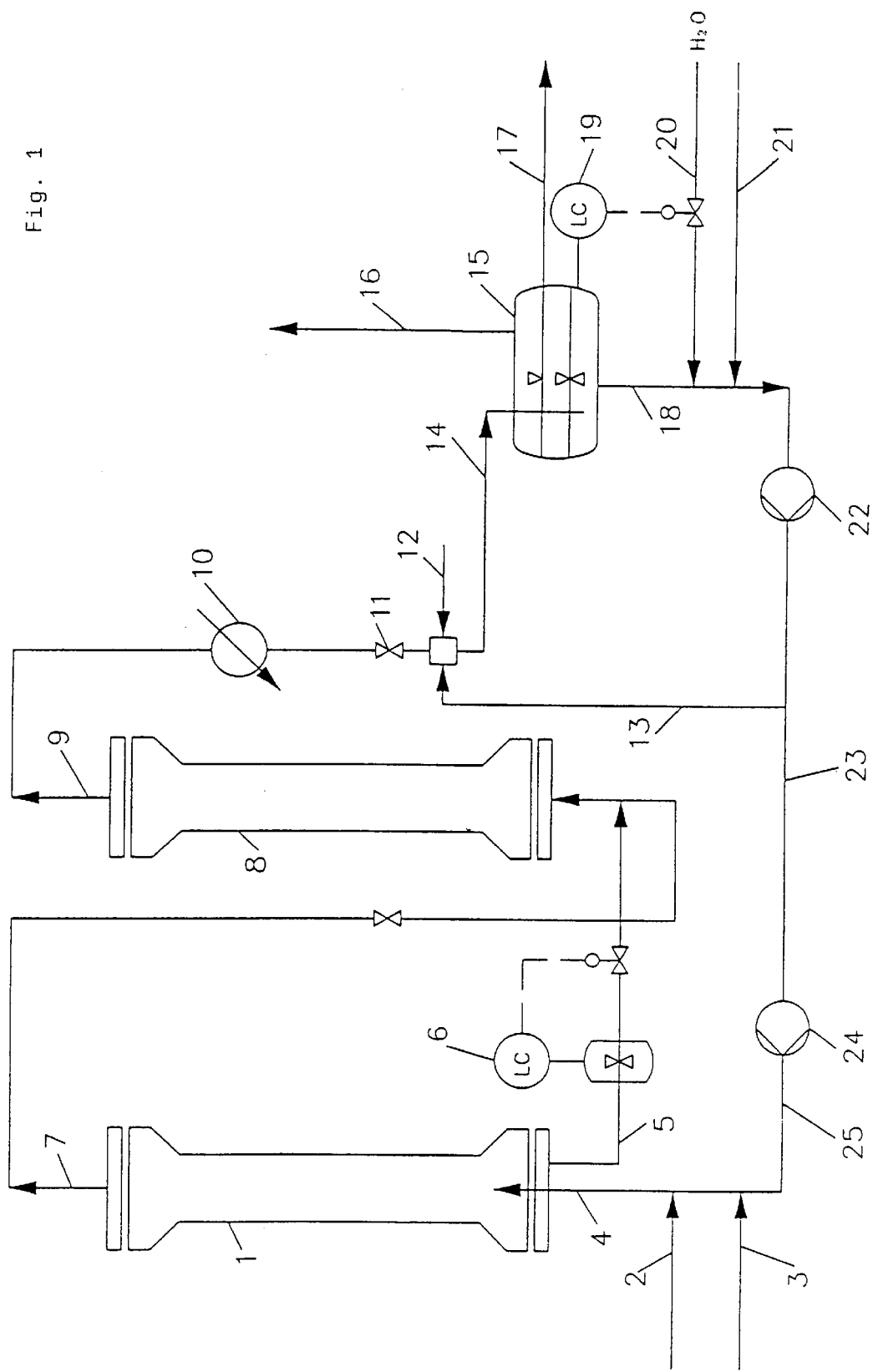

The process allows stable, trouble-free long-term operation.

9 Claims, 1 Drawing Sheet

CONTINUOUS PROCESS FOR HYDROFORMYLATING OLEFINS WITH 6 TO 20 CARBON ATOMS

Hydroformylation or the oxo process is an important industrial process and is employed for preparing aldehydes from olefins, carbon monoxide and hydrogen. These aldehydes can, if desired, be hydrogenated to the corresponding alcohols in the same operation or subsequently in a separate hydrogenation step using hydrogen. The hydroformylation is carried out in the presence of catalysts which are homogeneously dissolved in the reaction medium. Catalysts used are generally the carbonyl complexes of metals of transition group VIII, in particular Co, Rh, Ir, Pd, Pt or Ru, which can be unmodified or can be modified with, for example, amine- or phosphine-containing ligands. A review of processes carried out industrially may be found in J. Falbe, "New Syntheses with Carbon Monoxide", Springer Verlag 1980, p. 162 ff.

While short-chain olefins having up to 5 carbon atoms are at present hydroformylated using predominantly ligand-modified rhodium carbonyls as catalysts, in the case of longer-chain olefins cobalt has a dominant position as catalytically active central atom. This is due firstly to the high catalytic activity of the cobalt carbonyl catalyst regardless of the position of the olefinic double bonds, the branching structure and the purity of the olefin to be reacted. Secondly, the cobalt catalyst can be separated comparatively easily from the hydroformylation products and be returned to the hydroformylation reaction. In addition, catalyst losses during the work-up can be tolerated more readily because of the lower price of cobalt.

The known methods for separating off and recirculating the cobalt catalyst are based essentially on two principles: (1) no valence change takes place in the circuit, i.e. the cobalt remains in the formally negative monovalent form during the entire cycle of hydroformylation, separation and recirculation to the reactor; and (2) a valence change on the central atom from negative monovalent to metallic or positive divalent cobalt takes place in the circuit.

The prototype of principle (1) is the Kuhlmann process (cf. U.S. Pat. No. 3,188,351). In this process, the hydroformylation catalyst which is homogeneously dissolved in the reaction product and is in the form of hydridocobalt carbonyl is converted into its water-soluble sodium salt by means of sodium carbonate solution and is extracted into water. After phase separation, the volatile hydridocobalt carbonyl is liberated again from the aqueous alkaline solution by reaction with dilute sulfuric acid, stripped out by means of synthesis gas, taken up by the olefin to be reacted and returned to the reactor. However, owing to the instability of the hydridocobalt carbonyl and the large number of steps to be carried out successively, this process principle requires a number of expensive engineering precautions.

Processes based on principle (2), in which the organic phase of the reactor output is freed of the cobalt carbonyl complexes by treatment with oxygen or air in the presence of slightly acidic water (cf. DE-B 2404855), are simpler. Here, the cobalt catalyst is destroyed by oxidation and the central atom is formally converted from the oxidation state −1 to +2 and can then be removed by extraction with the aqueous solution. This step is also referred to as "oxidative decobalting". The cobalt complex required for the hydroformylation can be prepared again from the aqueous cobalt (II) salt solution by reaction with carbon monoxide and hydrogen. The cobalt catalyst produced is then extracted from the aqueous phase using an organic phase, preferably the olefin to be hydroformylated. Apart from the olefin, it is also possible to use the reaction products and by-products of the hydroformylation for the catalyst extraction. The olefins laden with the cobalt catalyst are then hydroformylated in a reactor under superatmospheric pressure and elevated temperature.

DE-A 2139630 describes a process for preparing predominantly straight-chain aldehydes by hydroformylation of olefinically unsaturated compounds, in which aqueous cobalt salt solutions are treated with carbon monoxide and hydrogen in a first stage, the aqueous solution is then extracted with an organic phase in a second stage and the organic phase and a mixture of carbon monoxide and hydrogen are transferred to a third stage where, if desired after introduction of the olefinically unsaturated compounds if they have not been used, or only part of them has been used, for the extraction in the second stage, the hydroformylation is carried out.

EP 0 850 905 describes a hydroformylation process in which the formation of the cobalt catalyst, the extraction of the cobalt catalyst formed into the organic phase and the hydroformylation of the olefins are carried out in a single-stage process in the hydroformylation reactor. The cobalt salt solution obtained after decobalting is circulated. In the examples of EP 0 850 905, the aqueous cobalt(II) salt solution used is an aqueous cobalt acetate solution containing 1% by weight of cobalt, calculated as metal. It has been found that when using such dilute aqueous cobalt(II) salt solutions, particularly when relatively long-chain olefins are employed, only a low loading of the olefins to be hydroformylated with active cobalt catalyst is achieved, since the volume of aqueous phase required for introducing higher amounts of cobalt can be dispersed only insufficiently in the organic reaction medium. This is reflected in unsatisfactory yields of the desired product.

However, when an attempt is made to use more highly concentrated aqueous cobalt salt solutions, e.g. cobalt acetate solution, it is found that stable, continuous operation over relatively long periods of time with complete recycling of the aqueous cobalt(II) salt solution is not possible without problems. Thus, precipitates of cobalt-containing salts in plant components carrying the aqueous cobalt salt solution are observed. The catalyst deficit has to be made up by continual introduction of fresh cobalt acetate solution. Consequently, part of the aqueous cobalt salt solution continually has to be taken from the circuit and worked up in a separate work-up step, e.g. by precipitation of cobalt hydroxide and dissolution of this in acetic acid, and returned to the process in concentrated form. This circuitous route is costly and associated with wastewater problems since cobalt ions damage the microorganisms in biological wastewater treatment plants.

It is an object of the present invention to hydroformylate olefins having from 6 to 20 carbon atoms continuously and in stable long-term operation in high yield on an industrial scale using aqueous cobalt(II) salt solutions in a process in which the catalyst circuit should be as simple as possible, largely loss-free and environmentally friendly.

The inventors have found that, regardless of the cobalt (II) salt originally used, the cobalt in the aqueous cobalt(II) salt solution is predominantly present as cobalt(II) formate after relatively long continuous operation. This is because formic esters of the alkanols having one more carbon atom than the olefins used are, in particular, formed as by-product of the cobalt-catalyzed hydroformylation. These are partly hydrolyzed in the reaction zone, with the formate anion going over into the aqueous cobalt(II) salt solution.

However, at ambient temperature cobalt(II) formate has a water solubility of only about 1% by weight, calculated as cobalt metal, i.e. the water solubility of cobalt(II) formate is less than a fifth of that of cobalt(II) acetate. A sufficient catalyst availability requires, however, more highly concentrated starting solutions.

The inventors have found that stable long-term operation using aqueous cobalt(II) formate solution having a concentration of from 1.1 to 1.7% by weight, based on cobalt, can be achieved if this is continually maintained under conditions under which the solubility limit of cobalt(II) formate in water is not exceeded.

The present invention accordingly provides a continuous process for the hydroformylation of olefins having from 6 to 20 carbon atoms, in which a) an aqueous cobalt(II) salt solution is brought into intimate contact with hydrogen and carbon monoxide to form a hydroformylation-active cobalt catalyst, (hereinafter also referred to as simply "cobalt catalyst") and the aqueous phase comprising the cobalt catalyst is brought into intimate contact with the olefins and, if desired, an organic solvent and also hydrogen and carbon monoxide in at least one reaction zone where the cobalt catalyst is extracted into the organic phase and the olefins are hydroformylated, b) the output from the reaction zone is treated with oxygen in the presence of acidic aqueous cobalt(II) salt solution, with the cobalt catalyst being decomposed to form cobalt(II) salts and these being backextracted into the aqueous phase; and the phases are subsequently separated, c) the aqueous cobalt(II) salt solution is recirculated in unchanged form to step a), wherein the cobalt(II) salt solution has a concentration of from 1.1 to 1.7% by weight, calculated as cobalt, and is continually maintained under conditions under which the solubility limit of cobalt(II) formate in water is not exceeded.

In other words, the cobalt(II) salt solution is continually maintained under conditions under which the solubility of cobalt(II) formate in water, calculated as cobalt, is at least as high as the concentration of the cobalt(II) salt in the aqueous cobalt(II) salt solution introduced into the process and is thus sufficiently high for the solution to be recirculated directly as catalyst precursor to the reaction zone and for stable long-term operation of the oxo process to be made possible. The conditions are preferably chosen so that the solubility is at least 1.3% by weight. This measure makes it possible to use relatively highly concentrated cobalt(II) salt solutions in the process and to circulate these continually without a renewed concentration step and without bleeding off substreams, without cobalt losses due to the process occurring in the catalyst circuit.

In the aqueous cobalt(II) salt solution circuit, the cobalt is present essentially as cobalt(II) formate in the process of the present invention. However, the hydroformylation plant can also be started up using, for example, cobalt acetylacetonate or the cobalt(II) salts of other carboxylic acids, e.g. cobalt acetate or cobalt ethylhexanoate.

The measures which lead to sufficient solubility of cobalt formate include, in particular, control of the pH of the cobalt(II) salt solution and/or the temperature of the cobalt (II) salt solution outside the reaction zone. Thus, the pH of the aqueous cobalt(II) salt solution is preferably maintained in the range from 2 to 4, in particular from 3 to 3.5. Maintenance of a pH in the range indicated prevents precipitation of basic cobalt(II) formates which are virtually water-insoluble and are consequently lost from the catalyst circuit. To maintain the specified pH, it is generally necessary to add acid, preferably formic acid, continuously or periodically to the aqueous cobalt(II) salt solution. The pH is preferably monitored continuously and the addition of acid is regulated according to need.

Furthermore, the aqueous cobalt(II) salt solution is preferably maintained at a temperature of at least 40° C., in particular from 60 to 95° C., outside the reaction zone. In a suitable embodiment, this is achieved by all plant components outside the reaction zone which in normal operation come into contact with the aqueous cobalt(II) salt solution being maintained at a temperature of at least 40° C., in particular from 60 to 95° C. For this purpose, it is generally necessary to provide sufficient insulation and possibly heating of the apparatuses and lines and also the instrumentation.

The concentration of the aqueous cobalt(II) salt solution is maintained in the range from 1.1 to 1.7% by weight, in particular from 1.3 to 1.5% by weight, calculated as cobalt. Owing to the water uptake capability of the hydroformylation product, a certain amount of water is continuously taken from the cobalt(II) salt solution circuit and separated off together with the organic phase in the phase separation in step b) (depending on chain length of the olefin to be hydroformylated, from 1 to 3%). To prevent an increase in concentration of the cobalt(II) salt solution and thus precipitation of cobalt(II) salts, the loss of water is preferably compensated for by continuous or periodic introduction of replacement water into the cobalt(II) salt solution circuit. This can be achieved in an elegant way by maintaining a constant level of the separation layer in the phase separation vessel in which the organic product phase which has been freed of the cobalt compounds is separated from the aqueous phase.

Step (a) of the process of the present invention comprises the stages of catalyst formation, catalyst extraction and hydroformylation. In the catalyst formation stage, the hydroformylation-active catalyst complex ($HCo(CO)_4$) is prepared from an aqueous cobalt(II) salt solution by reaction with carbon monoxide and hydrogen. In the catalyst extraction, the hydroformylation-active cobalt catalyst produced is extracted from the aqueous phase into the organic phase comprising the olefin to be hydroformylated and, if desired, the reaction products and by-products of the hydroformylation or any organic solvents used. The hydroformylation takes place in the organic phase laden with the cobalt catalyst, with the olefins being converted into aldehydes and/or alcohols having one more carbon atom.

In the process of the present invention, catalyst extraction and hydroformylation take place in one step in the reaction zone of the hydroformylation reactor. Catalyst formation can take place simultaneously therewith or in an earlier step. The prior formation of the catalyst outside the actual hydroformylation reactor is sometimes also referred to as precarbonylation. In the precarbonylation, the aqueous cobalt(II) salt solution is brought into contact with hydrogen and carbon monoxide in the absence of the olefins to be hydroformylated, preferably at from 50 to 200° C., in particular from 100 to 160° C., under pressures of from 100 to 400 bar, in particular from 200 to 300 bar. Customary apparatuses for gas-liquid reactions, e.g. stirred vessels with sparging stirrer, bubble columns or trickle bed columns, are suitable for this reaction. The precarbonylation is advantageously carried out in the presence of activated carbon, zeolites or basic ion exchangers which are laden with cobalt carbonyl, as described in DE-A 2139630. The resulting aqueous solution comprising cobalt(II) salts and cobalt catalyst is then conveyed together with the olefins to be hydroformylated and any organic solvents also used and also hydrogen and carbon monoxide to the reaction zone. Precarbonylation is advisable particularly in the hydroformylation of linear relatively long-chain olefins having terminal double bonds to prepare predominantly straight-chain aldehydes/alcohols. To minimize the formation of undesired branched hydroformylation products, relatively low reaction temperatures are generally employed here. Under these conditions, the active cobalt catalyst is not formed at a sufficient rate in the reaction zone of the hydroformylation reactor.

In many cases, it is preferable, because of the reduced process engineering complication, for the formation of the cobalt catalyst, the extraction of the cobalt catalyst into the organic phase and the hydroformylation of the olefins to be carried out in one step by bringing the aqueous cobalt(II) salt solution, the olefins and any organic solvent into intimate contact with one another in the reaction zone under hydroformylation conditions.

In this case, the starting materials are introduced into the reaction zone in such a way that good phase mixing occurs and a very high mass transfer area is generated. To meter the starting materials into the reaction zone, it is possible to use the metering devices known to those skilled in the art, for example packed turbulence tubes or mixing nozzles for multiphase systems. The metering-in is particularly preferably carried out using a mixing nozzle with maintenance of turbulent flow in the reaction zone. Thus, in a suitable embodiment, the bringing into intimate contact is achieved by introducing the aqueous cobalt(II) salt solution, olefin and also carbon monoxide and hydrogen simultaneously into a circulation system by means of a mixing nozzle, as described in DE-B 1205514 and 1938102. Any organic solvent also used is either present in the reaction zone or is introduced into the reaction zone simultaneously with the other starting materials, in particular by means of a mixing nozzle.

Suitable, pressure-rated reaction apparatuses for the hydroformylation are known to those skilled in the art. They include the generally customary reactors for gas-liquid reactions, e.g. tube reactors, stirred vessels, gas circulation reactors, bubble columns, etc., which may, if desired, be further divided by means of internals. An example of a suitable reactor is an upright high-pressure bubble column reactor which may, if desired, be provided with coaxial, tubular internals.

Carbon monoxide and hydrogen are usually used in the form of a mixture, known as synthesis gas. The composition of the synthesis gas used in the process of the present invention can vary within a wide range. The molar ratio of carbon monoxide to hydrogen is generally from about 10:1 to 1:10, in particular from 2.5:1 to 1:2.5. A preferred ratio is about 1:1.5.

Organic solvents which can, if desired, be used concomitantly are inert hydrocarbons such as paraffin fractions, aromatic hydrocarbons such as benzene, toluene or xylene, or an aldehyde and/or alcohol, in particular the hydroformylation product of the olefin used. Furthermore, it is possible to use high-boiling by-products of the hydroformylation as solvents. The concomitant use of a solvent can be advantageous for, for example, lowering the viscosity in the case of long-chain olefins.

The temperature in the hydroformylation is generally from 100 to 250° C., in particular from 145 to 200° C. The reaction is preferably carried out at a pressure in the range from 100 to 400 bar, in particular from 200 to 300 bar.

When using a vertical tube reactor, which can have internals as mentioned above, the reaction product is usually taken off at the top of the reactor. Particularly in the case of higher olefins having 9 carbon atoms or more, the aqueous phase which is fed to the reaction zone and is necessary to achieve a sufficient catalyst concentration in the reaction zone may sometimes be incompletely discharged in dissolved or suspended form together with the reaction mixture taken off at the top. This can lead to accumulation of aqueous phase in the reaction zone and to a gradual slowing and possibly to complete cessation of the hydroformylation reaction. For this reason, reaction product is, in a preferred embodiment, taken off both at the top of the reactor and also from the bottom zone of the reactor. The reaction product taken from the bottom zone preferably comprises from 10 to 80% by volume, in particular from 30 to 50% by volume, of aqueous phase. The takeoff of reaction product from the bottom zone is preferably phase-regulated. The amount taken off at the bottom is, depending on the cobalt concentration of the aqueous cobalt(II) salt solution and the chain length of the olefin to be hydroformylated, generally from about 10 to 40% by weight, based on the olefin used.

The stream taken off at the bottom of the hydroformylation zone comprises not only aqueous phase but also significant amounts of partially reacted organic phase. For this reason, with a view to achieving a yield of desired product which is as high as possible, the hydroformylation is preferably carried out in a reactor cascade. In a preferred embodiment, the reaction product taken off at the top of the reactor and that taken off from the bottom zone are therefore mixed and subjected once again to hydroformylation conditions in a second reaction zone. Alternatively, only the reaction product from the bottom zone may be fed to the second reaction zone. In the second reaction zone, fresh synthesis gas can be introduced if desired. Uniform transport of material from the first reaction zone to the second reaction zone is preferably achieved by maintaining a constant pressure differential of a few bar, e.g. from 2 to 5 bar.

The reaction product, which can, as mentioned, be subjected once again to hydroformylation conditions in a second reaction zone, is appropriately let down to intermediate pressure, generally from 10 to 30 bar, after leaving the reaction zone and is introduced into the decobalting stage. In the decobalting stage, the reaction product is freed of cobalt carbonyl complexes at preferably from 90 to 130° C. using air or oxygen in the presence of aqueous, slightly acidic cobalt(II) salt solution. The decobalting step can, if desired, be carried out in a pressure vessel packed with packing elements, e.g. Raschig rings, in which a very high mass transfer area is generated. In a downstream phase separation vessel, the organic product phase is separated from the aqueous phase. In the decobalting step, the hydroformylation-active cobalt catalyst is decomposed to form cobalt(II) salts, predominantly cobalt(II) formate. The cobalt(II) salts are backextracted into the aqueous phase. At the same time, the cobalt-depleted aqueous phase which remains after the catalyst extraction and is present in the reaction zone during the hydroformylation and passes together with the reaction product to the decobalting stage goes over into the aqueous cobalt(II) salt solution. The increase in concentration caused by back extraction of the cobalt(II) salts and the decrease in concentration caused by dilution with the cobalt-depleted aqueous phase essentially balance one another, so that the decobalting step gives a cobalt(II) salt solution having essentially the original concentration. According to the present invention, the aqueous cobalt(II) salt solution is recirculated in unchanged form, i.e. without chemical work-up or a concentration step, to the reaction zone or catalyst formation stage.

Subsequently, the organic phase remaining after the aqueous phase has been separated off can be worked up in an appropriate manner, e.g. be distilled and/or hydrogenated.

The process of the present invention makes it possible to hydroformylate olefins having from 6 to 20 carbon atoms. The process of the present invention is particularly suitable for the hydroformylation of isomeric olefin mixtures which are prepared by oligomerization of lower olefins such as propene and butenes.

Typical oligomers which are suitable as starting materials for the present process include, inter alia, dipropene, tripropene and tetrapropene, dibutene, tributene and tetrabutene and also mixed oligomers of propene and butenes. The oligomers of butenes are obtainable industrially by means of known oligomerization processes, e.g. the Octol® process of Hüls and the Dimersol® process of IFP. Furthermore, linear long-chain olefins having a terminal double bond, which are obtainable, for example, by means of the SHOP® process or Ziegler processes, or linear long-chain olefins having internal double bonds can also be hydroformylated by the process of the present invention.

A preferred embodiment of the invention will now be described in more detail with reference to FIG. 1 (attached). FIG. 1 schematically shows a plant suitable for carrying out the process of the present invention. Plant details which are self-evident per se and are not necessary for an understanding of the invention have been left out in the interest of clarity.

An upright high-pressure reactor 1 equipped with facilities for intensive mixing of the reactants and for removing the heat of reaction is supplied via lines 2, 3 and 25 with olefins ($\geq C_6$), synthesis gas and aqueous cobalt formate solution having a Co content of from 1.1 to 1.7% by weight.

The reaction product taken off at the top goes via line 7 to the after-reactor 8 which is likewise equipped with facilities for removing heat. A pressure drop of from 2 to 5 bar is set between the main reactor and the after-reactor. At the bottom of reactor 1, a part of the reactor contents is taken off via line 5 and combined with the feed stream to the after-reactor 8. This stream taken off at the bottom comprises, depending on the olefin used and on the concentration of the cobalt formate solution, from 10 to 80% of aqueous phase, with the remainder being organic phase. A particular phase ratio (e.g. 50:50) is maintained by means of the phase regulator 6.

The reaction mixture leaves the after-reactor 8 via line 9, passes through the cooler 10 and is let down from the reactor pressure (>200 bar) to intermediate pressure (from 10 to 30 bar) in the depressurization valve 11. Immediately after the pressure change, air is fed via line 12 and cobalt formate solution containing formic acid (cobalt content from 1.1 to 1.7% by weight) is fed via line 13 into the reaction product.

The three-phase mixture goes via line 14 to the separation vessel 15. The excess synthesis gas liberated leaves the plant via line 16. The organic upper phase which is essentially free of cobalt is taken off for further processing via line 17 and the aqueous phase is taken off via line 18. The phase interface regulator 19 continually supplies, via line 20, an amount of water corresponding to that carried out by the organic reaction product as a result of its water uptake capability.

The pump 22 conveys the aqueous cobalt formate solution (cobalt content from 1.1 to 1.7% by weight) via line 13 to the decobalting stage and via line 23 to the high-pressure pump 24. Finally, the reactor feed is admixed via line 25 with the required amount (about 0.13% by weight, based on olefin) of the 1.1–1.7 percent cobalt formate solution.

The cobalt circuit is completely closed. It is self-sufficient. There is no need to lead off a substream and carry out a separate work-up or concentration step. The minimal losses of at most about 3 ppm of cobalt (based on the organic reaction product) carried out together with the hydroformylation product have to be made up by occasional supplementary addition of concentrated cobalt(II) salt solution, e.g. 6 percent cobalt acetate solution, via line 21, as do losses caused by leakage, e.g. pumps.

The pH of the aqueous lower phase in the separation vessel 15 is monitored regularly and is kept in the range from 2 to 4 by addition of formic acid via line 21 as needed.

The lines 18, 13, 23 and 25 and the pumps 22 and 24 are provided with supplementary heating, e.g. in the form of electric heating tapes or pipes through which heating medium flows.

EXAMPLE 1

The process of the present invention is carried out in an industrial plant as shown schematically in FIG. 1.

The reactor 1 which is equipped with facilities for removal of heat and a mixing nozzle for mixing and for introducing the reactants into a circulation system has a utilizable reaction volume of 11.5 m$^3$ and the corresponding reaction volume of the after-reactor 8 is 8.5 m$^3$. The reaction conditions for the first reactor are 187°±1° C. and 275 bar. The temperature in the after-reactor is at the same level and the pressure is kept 3 bar below the pressure of the first reactor.

The reactor 1 is initially charged with crude nonanol and is then supplied with 4500 kg/h of an octene isomer mixture from the dimerization of butene by the IFP process together with 420 kg/h of an aqueous cobalt formate solution containing 1.4% by weight of cobalt and, pressure-regulated, 1460 kg/h of a synthesis gas mixture (CO content: 39.5 mol %).

The main part of the reaction mixture leaves the reactor 1 by the top and subsequently passes through the after-reactor 8. At the bottom of the reactor, about 500 kg/h of reactor contents are continuously taken off via the phase regulator 6 and are mixed into the feed to the after-reactor. This stream taken off at the bottom is, on average, 1/3 aqueous phase. The output from the after-reactor is cooled to below 150° C. in the heat exchanger 10 and is let down to about 20 bar in the depressurization valve 11.

Immediately after the pressure change, about 4000 kg/h of cobalt formate solution having a mean pH of 3 and 21 kg/h of air are mixed into the reaction product. The depressurization gas liberated is taken off from the phase separation vessel 15. The floating organic upper phase which has a residual cobalt content of from 1 to 2 ppm is continuously discharged and gives, after hydrogenation and distillation, 4940 kg/h of a pure i-nonyl alcohol mixture, corresponding to 85.4% of theory.

Due to its water uptake capability, the upper phase takes about 2% by weight of water from the aqueous catalyst system. This amount has to be continually replaced via the interface regulator 19 in order to maintain the cobalt concentration at 1.4%. The aqueous lower phase from the separation vessel 15 supplies, via the pump 22, the reaction product after depressurization with about 4000 kg/h of aqueous formate solution and the catalyst pump 24 with 420 kg/h of formate solution in order to form cobalt carbonyls in situ in the reactor.

At intervals of from 1 to 2 weeks, the cobalt carried out together with the organic phase and also leakage losses are made up by introduction of aqueous cobalt acetate solution containing 6% of Co via line 21. Additions of formic acid are also made via this line as required to keep the pH of the formate solution in the specified range of from 2 to 4 (on average about 5 kg/d of 100 percent of formic acid).

Comparative Example 1

This example is carried out using the same plant as in Example 1 but using a formate solution containing only 1% of cobalt instead of 1.4%.

At the same olefin feed rate as in Example 1, the amount of formate solution pumped to the reactor has to be increased to 590 kg/h. The amount of material taken off at the bottom of reactor 1 is doubled at approximately the same ratio of organic to aqueous phase (2:1). The remaining plant parameters remain essentially unchanged. The pure alcohol yield drops to 4700 kg/h, corresponding to 81.4% of theory.

Comparative Example 2

The settings of Comparative Example 1 are adopted; in addition, the bottom outlet from reactor 1 is closed.

After only a few hours, a significant decrease in synthesis gas consumption is observed. To maintain the reaction to some extent, the reaction temperature has to be increased to >190° C. The output from the reactor still contains considerable amounts of unreacted or hydrogenated feed olefin. The pure alcohol yield drops to about 2500 kg/h, corresponding to 43.2% of theory.

EXAMPLE 2

The process of the present invention is carried out in the industrial plant described in Example 1.

The reaction conditions for the first reactor are 192±1° C. and 275 bar. The temperature in the after-reactor is at the same level, while the pressure is kept 3 bar below that of the first reactor.

The reactor 1 is initially charged with crude tridecanol and is supplied with 3500 kg/h of a dodecene isomer mixture from the trimerization of butene by the IFP process together with 310 kg/h of an aqueous cobalt formate solution containing 1.5% by weight of cobalt and, pressure-regulated, 790 kg/h of a synthesis gas mixture (CO content: 39.5 mol %).

The plant is operated as in Example 1 and about 500 kg/h of reactor contents, ⅓ of which is water, are taken, phase-regulated, from the bottom of reactor 1. Otherwise, the procedure is analogous to that of Example 1.

After hydrogenation and distillation, the organic upper phase gives 3350 kg/h of a pure tridecanol isomer mixture, corresponding to 80.4% of theory.

Here too, as already described in Example 1, the interface regulator 19 for the separation vessel 15 automatically maintains the cobalt concentration of the formate solution, in this case 1.5%; owing to the reduced water uptake capability of the $C_{13}$ hydroformylation product, somewhat less water has to be replaced.

We claim:
1. A continuous process for the hydroformylation of olefins having from 6 to 20 carbon atoms, in which
   a) an appliance is provided, which optionally comprises a catalyst formation zone, and comprises at least one reaction zone, an extraction zone, conveying means for conveying the output from the reaction zone to the extraction zone and recirculation means for recirculating an aqueous cobalt(II) salt solution emanating from the extraction zone back to the catalyst formation zone or the reaction zone, the recirculation zone means being thermally insulated and/or provided with heating means such that the aqueous cobalt(II) salt solution conveyed therein is maintained at a temperature of from 60 to 95° C.,
   b) the aqueous cobalt(II) salt solution having a concentration of from 1.1 to 1.7% by weight, calculated as cobalt, and a pH in the range from 2 to 4, is brought into intimate contact with hydrogen and carbon monoxide in the catalyst formation zone or the reaction zone, to form a hydroformylation-active cobalt catalyst,
   c) the aqueous phase comprising the cobalt catalyst is brought into intimate contact with the olefins and, if desired, an organic solvent and also hydrogen and carbon monoxide in the reaction zone where the cobalt catalyst is extracted into the organic phase and the olefins are hydroformylated,
   d) The output from the reaction zone is conveyed to the extraction zone and treated with oxygen in the presence of acidic aqueous cobalt(II) salt solution, and the cobalt catalyst being decomposed to form cobalt (II) salts and these being back extracted into the aqueous phase and the phases are subsequently separated,
   e) the aqueous cobalt(II) salt solution is recirculated in unchanged form to step b).

2. A process as claimed in claim 1, wherein the pH is adjusted by addition of formic acid.

3. A process as claimed in claim 1, wherein the water which dissolves in the organic phase and is removed from the aqueous cobalt(II) salt solution is replaced continuously or periodically.

4. A process as claimed in claim 1, wherein the formation of the cobalt catalyst, the extraction of the cobalt catalyst into the organic phase and the hydroformylation of the olefins are carried out in one step by bringing the aqueous cobalt(II) salt solution, the olefins and any organic solvent and also hydrogen and carbon monoxide into intimate contact with one another in the reaction zone under hydroformylation conditions.

5. A process as claimed in claim 4, wherein the bringing into intimate contact is achieved by introducing the aqueous cobalt(II) salt solution, the olefins and any organic solvent and also carbon monoxide and hydrogen into the reaction zone by means of a mixing nozzle.

6. A process as claimed in claim 1, wherein the reaction zone is a vertical tube reactor and the reaction product is taken off both at the top of the reactor and also from the bottom zone of the reactor.

7. A process as claimed in claim 6, wherein the reaction product taken from the bottom zone comprises from 10 to 80% by volume of aqueous phase.

8. A process as claimed in claim 6, wherein the reaction product taken off at the top of the reactor and that taken off from the bottom zone of the reactor are mixed and subjected once again to hydroformylation conditions in a second reaction zone.

9. A process as claimed in claim 1, wherein the cobalt in the aqueous cobalt(II) salt solution is present essentially as cobalt(II) formate.

* * * * *